(12) United States Patent
Lauf et al.

(10) Patent No.: US 9,993,347 B2
(45) Date of Patent: Jun. 12, 2018

(54) SUBTALAR IMPLANTS

(71) Applicant: Life Spine, Inc., Huntley, IL (US)

(72) Inventors: Garrett D. Lauf, Elgin, IL (US); Michael S. Butler, St. Charles, IL (US); Matthew S. Coyne, Naperville, IL (US)

(73) Assignee: Life Spine, Inc., Huntley, IL (US)

( * ) Notice: Subject to any disclaimer, the term of this patent is extended or adjusted under 35 U.S.C. 154(b) by 0 days. days.

(21) Appl. No.: 15/256,587

(22) Filed: Sep. 4, 2016

(65) Prior Publication Data

US 2017/0065423 A1 Mar. 9, 2017

Related U.S. Application Data

(60) Provisional application No. 62/214,883, filed on Sep. 4, 2015, provisional application No. 62/259,938, filed on Nov. 25, 2015.

(51) Int. Cl.
*A61F 2/42* (2006.01)
*A61B 17/68* (2006.01)
*A61B 17/84* (2006.01)
*A61F 2/30* (2006.01)

(52) U.S. Cl.
CPC ............ *A61F 2/4202* (2013.01); *A61B 17/68* (2013.01); *A61B 17/844* (2013.01); *A61F 2002/30405* (2013.01); *A61F 2002/30433* (2013.01); *A61F 2002/30579* (2013.01); *A61F 2002/4207* (2013.01)

(58) Field of Classification Search
CPC ........................ A61F 2/4202; A61F 2002/4207
See application file for complete search history.

(56) References Cited

U.S. PATENT DOCUMENTS

| 5,360,450 A | 11/1994 | Giannini |
| 2008/0208349 A1 | 8/2008 | Graser |
| 2011/0071579 A1 | 3/2011 | Reach |
| 2012/0245701 A1* | 9/2012 | Zak ................. A61F 2/4202 623/21.18 |

FOREIGN PATENT DOCUMENTS

| EP | 2213263 | 8/2010 |
| EP | 2567677 | 3/2013 |

OTHER PUBLICATIONS

Search Report and Written Opinion for International Application No. PCT/US2016/050319, dated Nov. 29, 2016, 8 pages.

* cited by examiner

Primary Examiner — Jason-Dennis Stewart
(74) Attorney, Agent, or Firm — Foley & Lardner LLP

(57) ABSTRACT

The invention is a subtalar implantable to expand after implantation. The subtalar implant has two or more expansion segments or wings. In all forms, the expansion wings are hinged on the distal portion of the subtalar implant which causes only the proximal portion of the wing to expand relative to the midplane of the implant. The expansion wings and the entire subtalar implant are threaded to prevent the implant from backing out of the sinus tarsi once implanted. In one form, the subtalar implant includes an integral expansion screw that, when rotated, expands the expansion wings. In another form, the subtalar implant includes a separate expansion screw that, when rotated, expands the expansion wings. The integral and the separate expansion screw includes a socket that accepts a like driver tool for rotating the expansion screw and expanding the expansion wings.

20 Claims, 15 Drawing Sheets

SUBTALAR IMPLANTS

CROSS-REFERENCE TO RELATED APPLICATIONS

This U.S. non-provisional patent application claims the benefit of and/or priority under 35 U.S.C. § 119(e) to U.S. provisional patent application Ser. No. 62/214,883 filed Sep. 4, 2015 titled "Subtalar Implants," and U.S. provisional patent application Ser. No. 62/259,938 filed Nov. 25, 2015, titled "Subtalar Implant," the entire contents of each of which is specifically incorporated herein by reference.

FIELD OF THE INVENTION

The present invention relates to orthopedic implants for the foot and, particularly, to subtalar implants.

BACKGROUND OF THE INVENTION

There are various issues that can arise with respect to the bones of the foot. Such issues can be a congenital or acquired deformity or abnormality of one or more bones of the foot, a disease or trauma affecting one or more bones of the foot, or other foot bone issue. While some conditions or issues can be alleviated without surgery, other issues respond better to surgery. In some cases, surgery may include installing an orthopedic implant.

Arthroereisis (also referred to as arthroisis) is a limitation of excessive movement across a bone joint of the foot. Subtalar arthroereisis is designed to correct excessive talar displacement and calcaneal eversion by reducing pronation across the subtalar joint. Extraosseous talotarsal stabilization is also being evaluated as a treatment of talotarsal joint dislocation. It is performed by placing an implant in the sinus tarsi, which is a canal located between the talus and the calcaneous.

While numerous implants have been developed over the years to correct excessive talar displacement and calcaneal eversion, they are deficient in many respects. It is therefore an object of the present invention to provide a subtalar implant that overcomes the deficiencies of the prior art.

SUMMARY OF THE INVENTION

The invention is a subtalar implant that is able to expand after implantation into the sinus tarsi in order to correct excessive talar displacement and calcaneal eversion. The present subtalar implant is used to treat a wide range of flat foot and other foot disorders.

In one form, the subtalar implant has two expansion segments or wings. In this form, the two expansion segments are preferably, but not necessarily, situated 180° apart. In another form, the subtalar implant has four expansion segments or wings. In this form, the four expansion segment are preferably, but not necessarily, situated 90° apart. In both forms, other spacing of the expansion segments are contemplated. This can include equal and non-equal spacing. Additionally, subtalar implants having three expansion segments or more than four expansion segments are contemplated.

In all forms, the expansion wings are hinged on the distal portion of the subtalar implant, which causes only the proximal portion of the wing to expand relative to the midplane of the implant. The expansion wings and the entire subtalar implant are threaded to prevent the implant from backing out of the sinus tarsi once implanted.

In one form, the subtalar implant includes an integral expansion screw that, when rotated, expands the expansion wings. The integral expansion screw includes a hex (or other style) socket that accepts a like driver tool for engaging the hex socket and rotating the expansion screw.

In one form, the subtalar implant includes a separate expansion screw that, when rotated, expands the expansion wings. The separate expansion screw includes a hexalobe (or other style) socket that accepts a like driver tool for engaging the hexalobe socket and rotating the expansion screw.

In all forms, the subtalar implant has cutouts on the side of the implant body that allow an installer to grasp the implant and install it. An inner shaft of the implant has a hex socket that allows a hex driver to expand the wings of the implant after the implant is placed in the sinus tarsi.

According to one method of use, the subtalar implant is inserted into the lateral aspect of the sinus tarsi using a driver to grasp the implant via its cutouts and rotating the subtalar implant clockwise. After the subtalar implant is placed into the lateral aspect of the sinus tarsi, a hex driver is then placed into the hex socket of the expansion screw in order to expand the implant to obtain the necessary height and prevent the implant from backing out.

In another method of use, the subtalar implant is inserted into the lateral aspect of the sinus tarsi using a driver to grasp the implant via its cutouts and rotating the subtalar implant clockwise. After the subtalar implant is placed into the lateral aspect of the sinus tarsi, a separate expansion screw is inserted into the implant. A hex driver is then placed into a hex socket of the separate expansion screw in order to expand the implant to obtain the necessary height and prevent the implant from backing out.

Further aspects of the present invention will become apparent from consideration of the drawings and the following description of forms of the invention. A person skilled in the art will realize that other forms of the invention are possible and that the details of the invention can be modified in a number of respects without departing from the inventive concept. The following drawings and description are to be regarded as illustrative in nature and not restrictive.

BRIEF DESCRIPTION OF THE DRAWINGS

The features of the invention will be better understood by reference to the accompanying drawings which illustrate forms of the present invention, wherein.

DETAILED DESCRIPTION OF THE INVENTION

Referring to FIGS. 1-8, there is depicted an exemplary form of the present subtalar implant, generally designated 10. The subtalar implant 10 is made from a biocompatible material such as, but not limited to, titanium, stainless steel, an alloy of titanium or steel, or other. The subtalar implant is characterized by a body 12 in the general shape of an ogive, having a majority, if not all, of the outer surface thereof covered in threading, serrations or the like. The subtalar implant 10 includes an integral internal expansion mechanism as described below.

Figure 1:
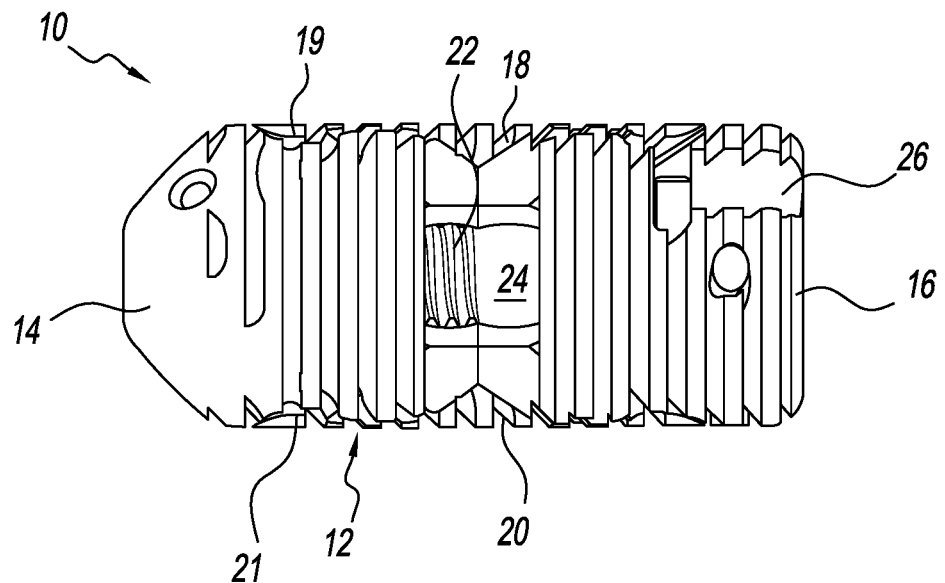
FIG. 1 is a side view of one form of an expandable subtalar implant fashioned in accordance with the present principles, the expandable subtalar implant having two expansion segments that are in an unexpanded state.
Figure 2:
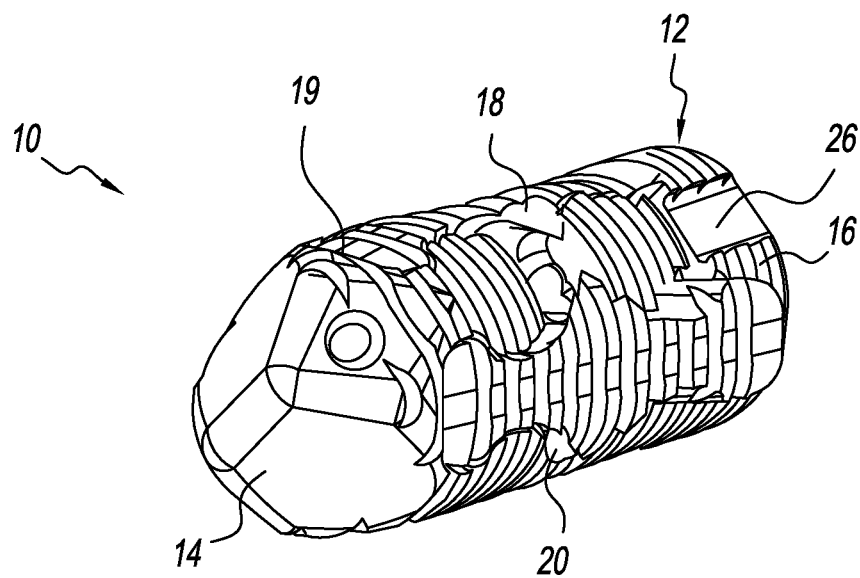
FIG. 2 is a front side isometric view of the expandable subtalar implant of FIG. 1 with the two expansion segments in the unexpanded state.
Figure 3:
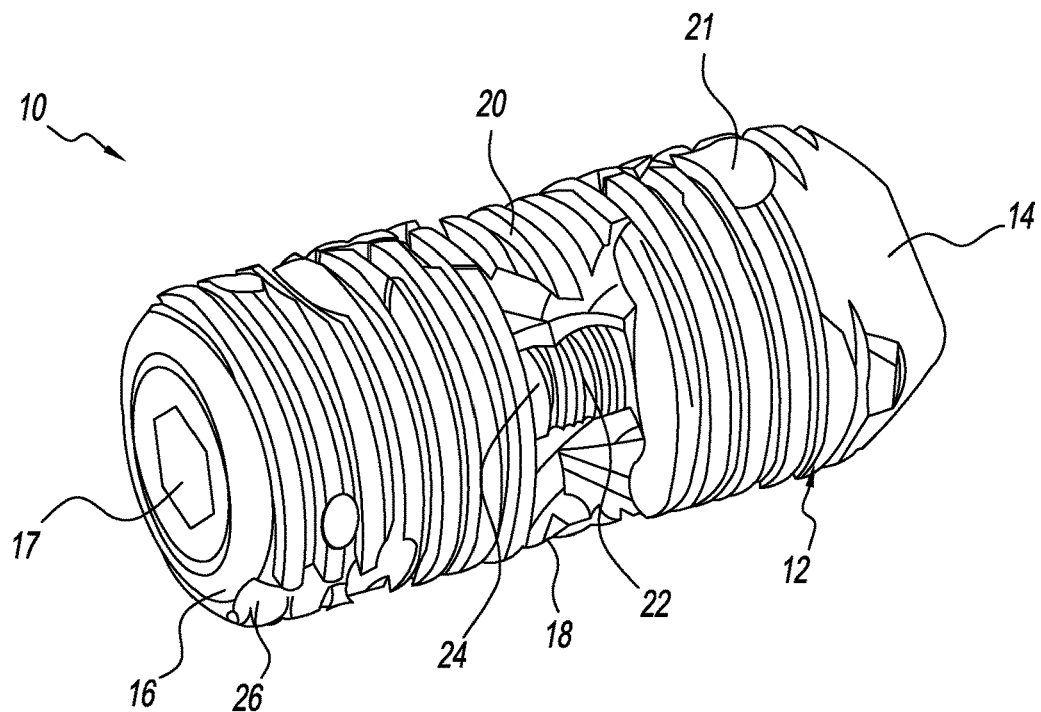
FIG. 3 is a rear side isometric view of the expandable subtalar implant of FIG. 1 with the two expansion segments in the unexpanded state.
Figure 4:
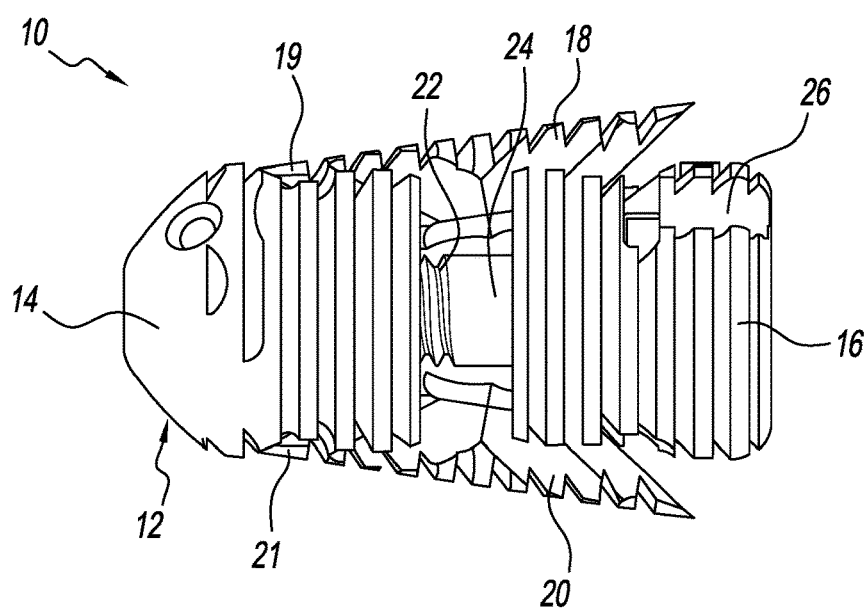
FIG. 4 is a side view of the expandable subtalar implant of FIG. 1 with the two expansion segments in an expansion state.
Figure 5:
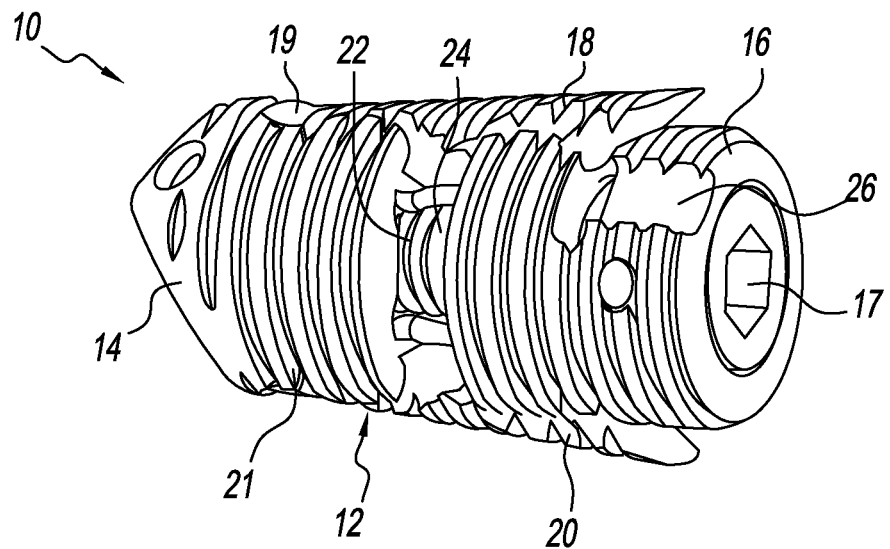
FIG. 5 is a rear side view of the expandable subtalar implant of FIG. 1 with the two expansion segments in an expansion state.
Figure 6:
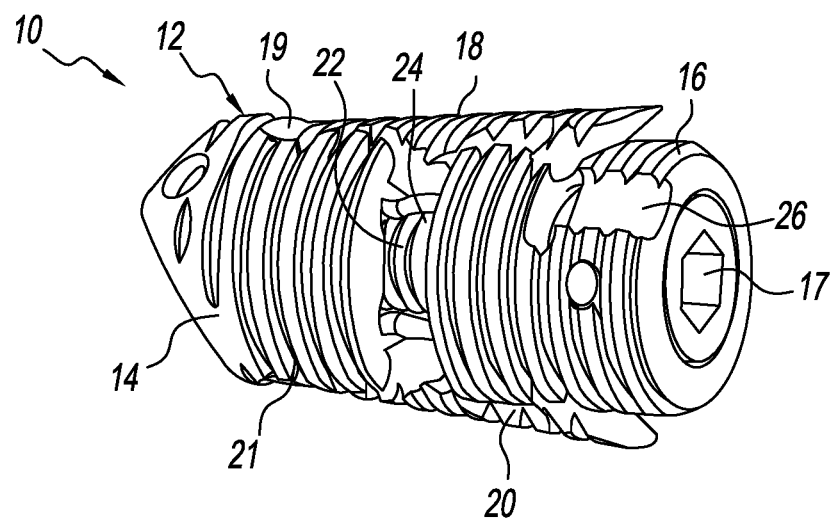
FIG. 6 is a rear side view of the expandable subtalar implant of FIG. 1 with the two expansion segments in an expansion state.
Figure 7:
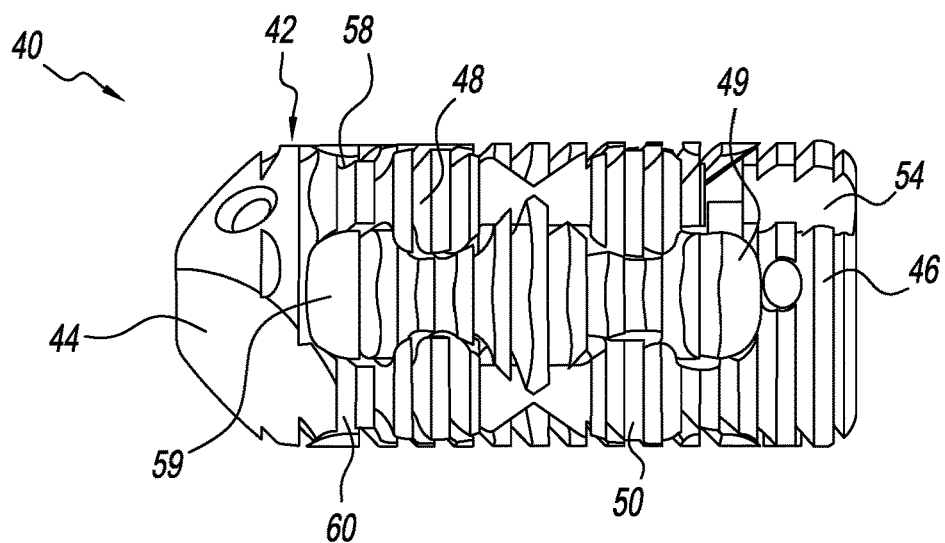
FIG. 7 is a side view of the expandable subtalar implant of FIG. 1 with the two expansion segments in an unexpanded state.
Figure 8:
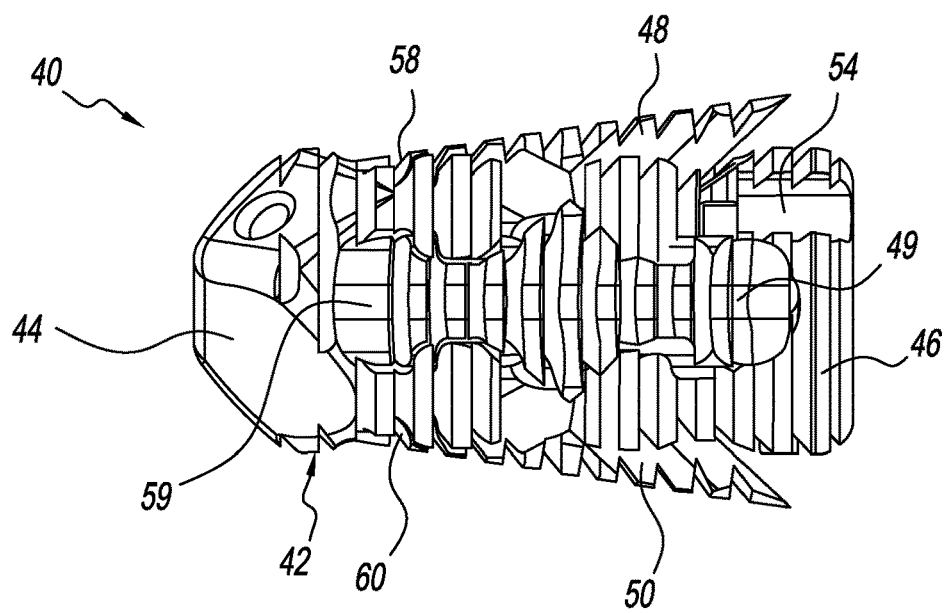
FIG. 8 is a side view of the expandable subtalar implant of FIG. 1 with the two expansion segments in an expanded state.

The body 12 has a head 14 in the general shape of an arc at a distal end of the implant that aids in insertion of the implant 10. A first wing or expansion segment 18 is provided along the outside surface of the body 12, the first wing 18 having a long axis that is co-axial with a long axis of the body 12. The distal end of the first wing 18 is hinged 19 to the body 12 such that the first wing 18 can expand, elevate or pivot from the body 12. A second wing or expansion segment 20 is provided along the outside surface of the body 12, the second wing 20 having a long axis that is co-axial with a long axis of the body 12, the nomenclature first and second being arbitrary. The distal end of the second wing 20 is hinged 21 to the body 12 such that the second wing 20 can expand, elevate or pivot from the body 12. In FIGS. 1-3 the first and second wings 18, 20 are in an unexpanded or un-pivoted position (i.e. an unexpanded state) while in FIGS. 4-8 the first and second wings 18, 20 are in expanded or pivoted positions (i.e. expanded states). The amount of expansion or pivoting of the first and second wings 18, 20, and thus the amount of expansion of the implant 10 is controlled as described below.

The implant 10 includes a screw drive that is internal to the body 12. The screw drive incudes a threaded shaft 22 that is connected at an upper end thereof to an inside distal area of the body 12. An expander 16 of the screw drive is situated inside the body 12. The expander 16 is an externally threaded piece disposed generally at the proximate end of the body 12 and having an internally threaded boss 24 that is situated on the threaded shaft 22. A socket 17 is provided in the end of the expander 16 for receipt of a drive tool (not shown) in order to rotate the expander 16. While the socket 17 is shown as a hexagon (for receipt of a hex driver), other shapes and like drivers may be used. The expander 16 is rotatable on the threaded shaft 22 such that rotation in one direction advances the expander further into the body 12 while rotation in another direction regresses the expander out of the body 12.

The first wing 18 includes threading along its inside surface. The second wing 20 also includes threading along its inside surface. The external threading of the expander 16 meshes with the inside threading of the first and second wings 18, 20. Rotation of the expander 16 to advance the expander 16 into the body 12 spreads or expands the first and second wings 18, 20 such that the first and second wings 18, 20 pivot outwardly at their hinges 19, 21 thereby expanding the implant 10. The amount of expansion of the wings is dependent upon how far the expander 16 is advanced into the body 12. Opposite rotation of the expander 16 regresses the expander 16 from the body 12 and allows the first and second wings 18, 20 to un-expand or collapse back into the body 12.

The expander 16 further includes first and second cutouts 26, 28 on an outside surface thereof, the nomenclature first and second being arbitrary. The first and second cutouts 26, 28 allow the user to grasp the implant 10 for implanting.

Figure 9:
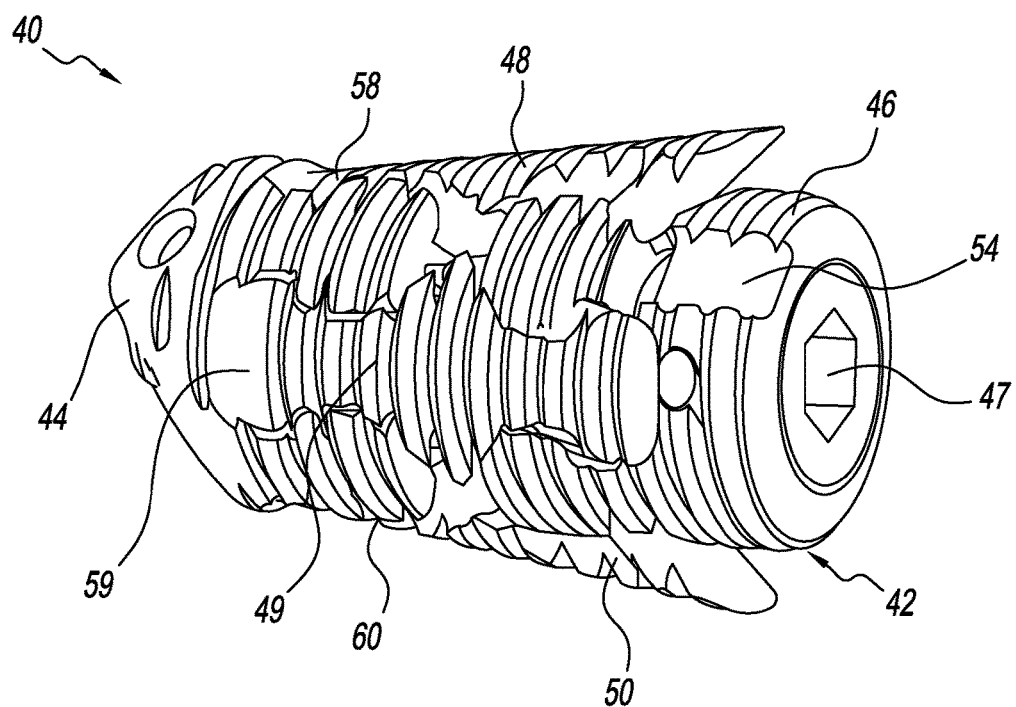
FIG. 9 is a side rear view of another form of an expandable subtalar implant fashioned in accordance with the present principles, the expandable subtalar implant having four expansion segments that are in an unexpanded state.
Figure 10:
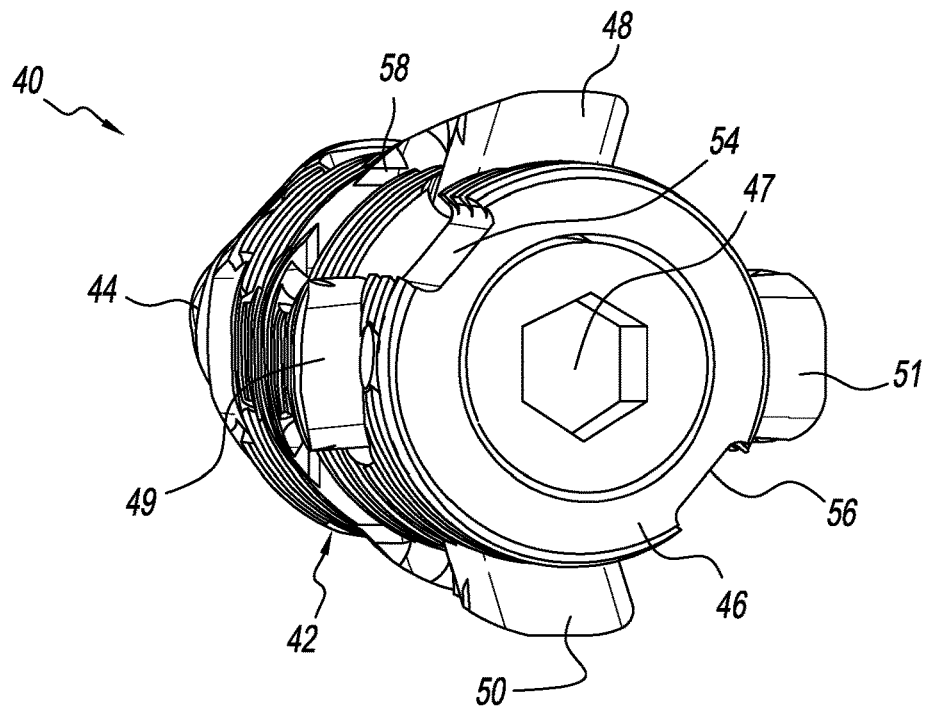
FIG. 10 is a rear isometric view of the expandable subtalar implant of FIG. 9 with the four expansion segments in an expansion state.
Figure 11:
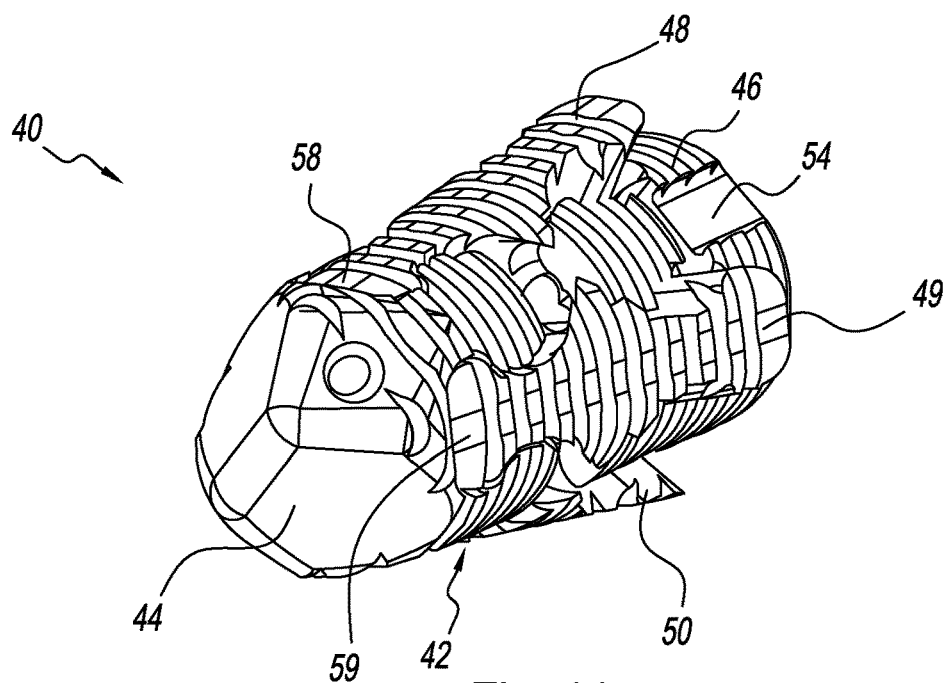
FIG. 11 is a front side isometric view of the expandable subtalar implant of FIG. 9 with the four expansion segments in an expansion state.

Referring to FIG. 9-11, there is depicted another exemplary form of the present subtalar implant generally designated 40. The subtalar implant 40 is made from a biocompatible material such as, but not limited to, titanium, stainless steel, an alloy of titanium or steel, or other. The subtalar implant is characterized by a body 42 in the general shape of an ogive, having a majority, if not all, of the outer surface thereof covered in threading, serrations or the like.

The body 42 has a head 44 in the general shape of an arc at a distal end of the implant that aids in insertion of the implant 40. A first wing or expansion segment 48 is provided along the outside surface of the body 42, the first wing 48 having a long axis that is co-axial with a long axis of the body 42. The distal end of the first wing 48 is hinged 58 to the body 42 such that the first wing 48 can expand, elevate or pivot from the body 42. A second wing or expansion segment 49 is provided along the outside surface of the body 42, the second wing 49 having a long axis that is co-axial with a long axis of the body 42. The distal end of the second wing 49 is hinged 59 to the body 42 such that the second wing 49 can expand, elevate or pivot from the body 42. A third wing or expansion segment 50 is provided along the outside surface of the body 42, the third wing 50 having a long axis that is co-axial with a long axis of the body 42. The distal end of the third wing 50 is hinged 60 to the body 42 such that the third wing 50 can expand, elevate or pivot from the body 42. A fourth wing or expansion segment 51 is provided along the outside surface of the body 42, the fourth wing 51 having a long axis that is co-axial with a long axis of the body 42. The distal end of the fourth wing 51 is hinged 61 to the body 42 such that the fourth wing 51 can expand, elevate or pivot from the body 42. The nomenclature first, second, third and fourth being arbitrary. The amount of expansion or pivoting of the first, second, third and fourth wings 48, 49, 50, 51, and thus the amount of expansion of the implant 40 is controlled as described below.

The implant 40 includes a screw drive that is internal to the body 42. The screw drive incudes a threaded shaft that is connected at an upper end thereof to an inside distal area of the body 42. An expander 46 of the screw drive is situated inside the body 42. The expander 46 is an externally threaded piece disposed generally at the proximate end of the body 42 and having an internally threaded boss that is situated on the threaded shaft. A socket 47 is provided in the end of the expander 46 for receipt of a drive tool (not shown) in order to rotate the expander 46. While the socket 47 is shown as a hexagon, hexalobe or the like (for receipt of a hex/hexalobe driver), other shapes and like drivers may be used. The expander 46 is rotatable on the threaded shaft such that rotation in one direction advances the expander further into the body 42 while rotation in another direction regresses the expander out of the body 42.

The first, second, third, and fourth wings 48, 49, 50, 51 include threading along their inside surface. The external threading of the expander 46 meshes with the inside threading of the first, second, third, and fourth wings 48, 49, 50, 51. Rotation of the expander 46 to advance the expander 46 into the body 42 spreads or expands the first, second, third, and fourth wings 48, 49, 50, 51 such that the first, second, third, and fourth wings 48, 49, 50, 51 pivot outwardly at their hinges 58, 59, 60, 61 thereby expanding the implant 40. The amount of expansion of the wings is dependent upon how far the expander 46 is advanced into the body 42. Opposite rotation of the expander 46 regresses the expander 46 from the body 42 and allows the first, second, third, and fourth wings 48, 49, 50, 51 to un-expand or collapse back into the body 42. The expander 46 further includes first and second cutouts 54, 56 on an outside surface thereof, the nomenclature first and second being arbitrary. The first and second cutouts 54, 56 allow the user to grasp the implant 40 for implanting.

Figure 12:
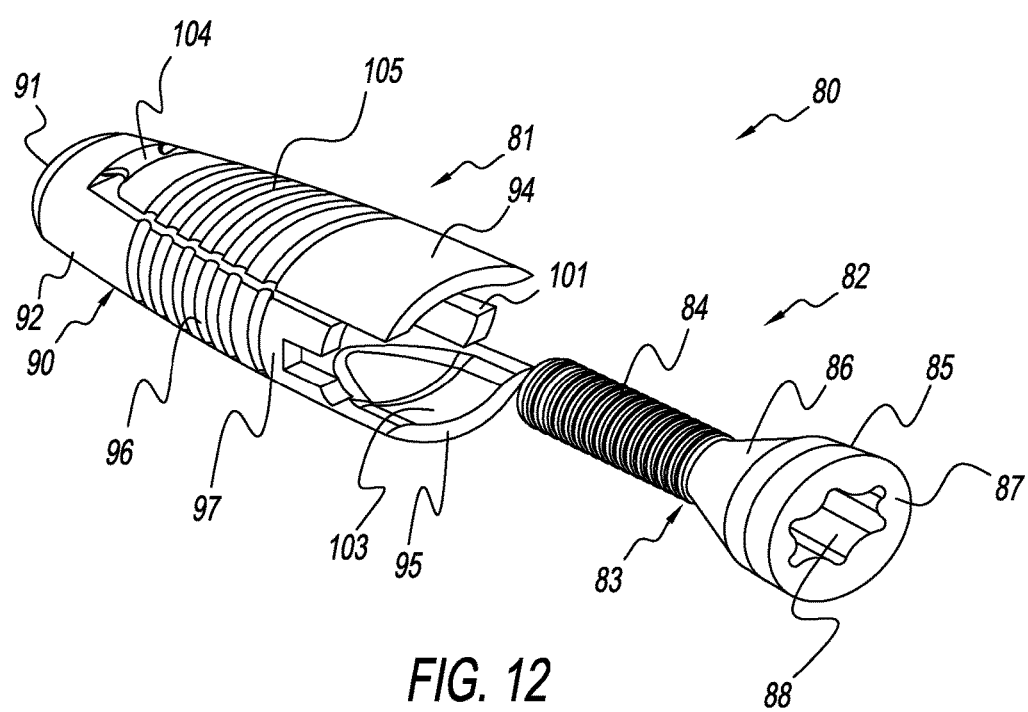
FIG. 12 is an exploded view of another form of an expandable subtalar implant fashioned in accordance with the present principles, the expandable subtalar implant having two expansion segments that are in an unexpanded state.
Figure 13:
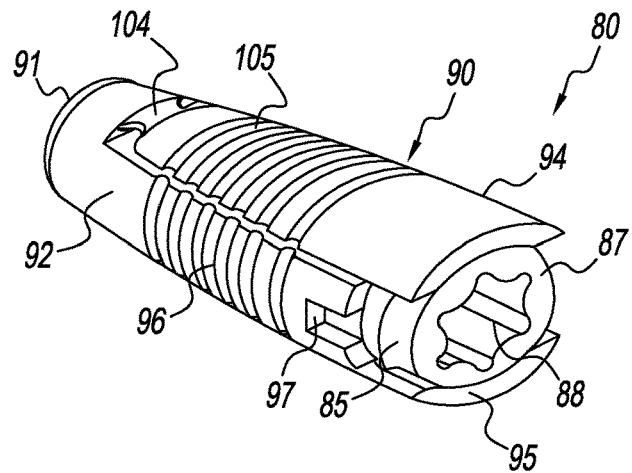
FIG. 13 is a rear isometric view of the subtalar implant of FIG. 12, the two expansion segments in an unexpanded state.
Figure 14:
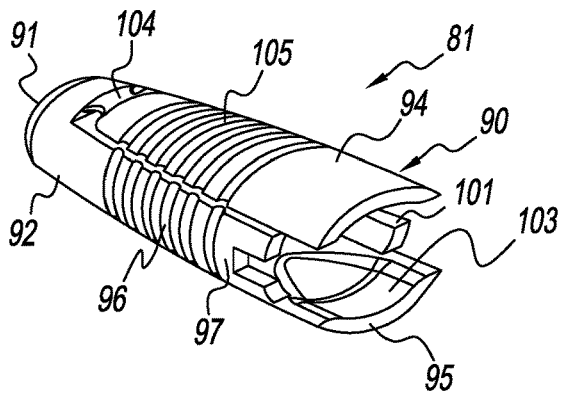
FIG. 14 is a rear isometric view of a component of the subtalar implant of FIG. 12.
Figure 15:
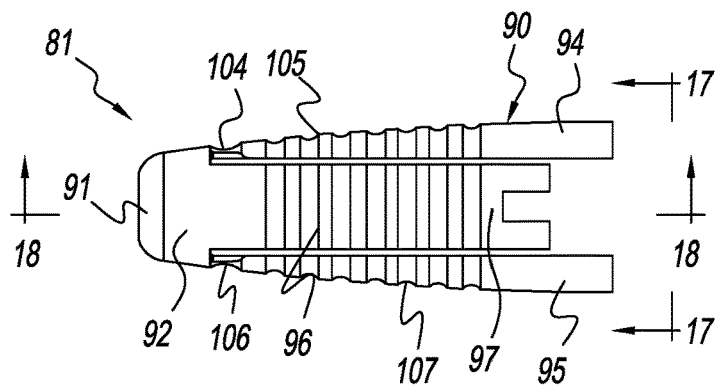
FIG. 15 is a side view of the component of FIG. 14.
Figure 16:
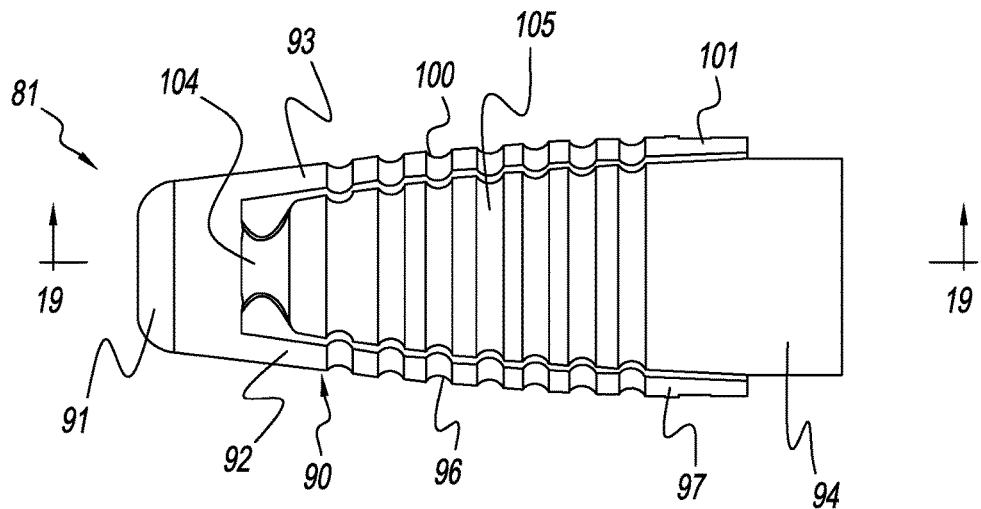
FIG. 16 is another side view of the component of FIG. 14.
Figure 17:
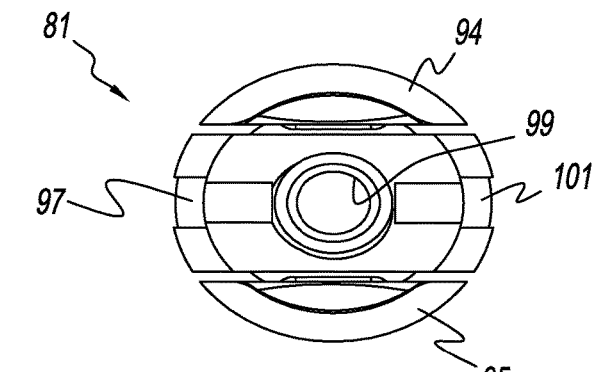
FIG. 17 is an end view of the component of FIG. 14 taken along line 17-17 of FIG. 15.
Figure 18:
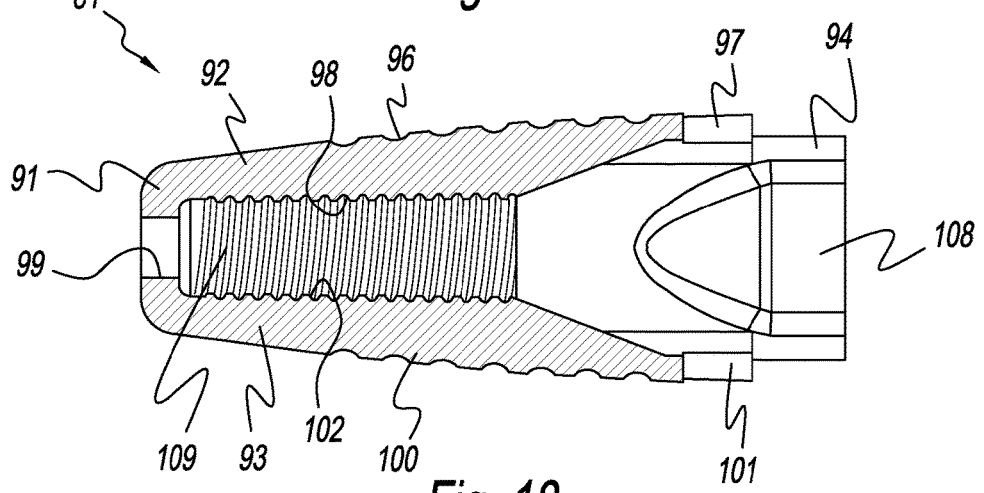
FIG. 18 is a sectional view of the component of FIG. 14 taken along line 18-18 of FIG. 15.
Figure 19:
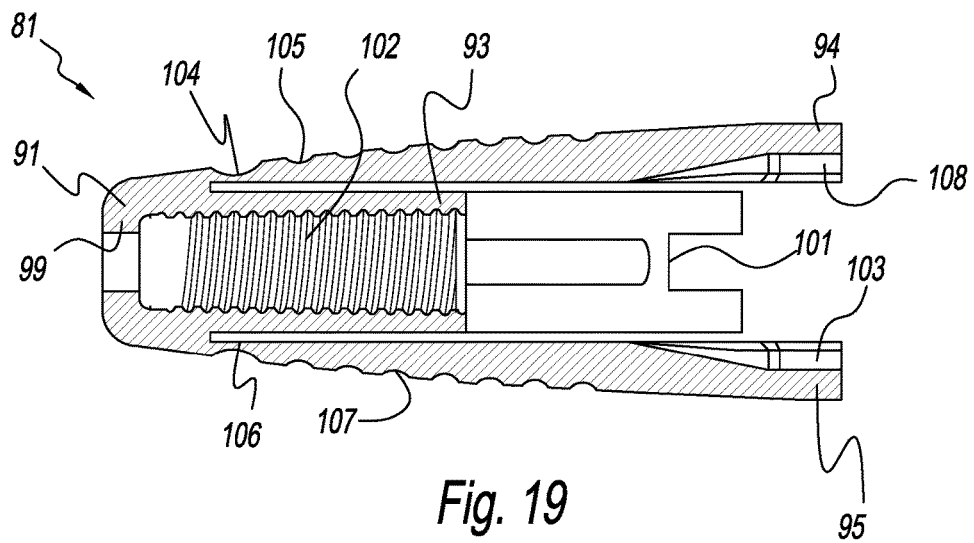
FIG. 19 is a sectional view of the component of FIG. 14 taken along line 19-19 of FIG. 16.

Referring to FIGS. 12-33, there is depicted various views of another exemplary form of the present subtalar implant, generally designated 80 and its components. The subtalar implant 80 is made from a biocompatible material such as, but not limited to, titanium, stainless steel, an alloy of titanium or steel, or other. The subtalar implant is characterized by a first component 81 and a second component 82. The first component 81 is in the general shape of an ogive and may be considered an implant body 81. The second component 82 is a separate expansion mechanism or member and is embodied in this form as a screw 82. FIG. 12 shows the expansion screw 82 separate from the implant body 81, the implant body in an unexpanded state. FIG. 13 depicts the expansion screw 82 inserted in the implant body 81, the implant body 81 in the unexpanded state.

The implant body 81 of the subtalar implant 80 is more particularly shown in FIGS. 14-19 in an unexpanded, normal or unbiased state before insertion of the expansion screw 82. The implant body 81 has a generally conical or ogive configuration 90 having a nose or end 91. A first portion or arm 92 extends from one side of the nose 91, while a second portion or arm 93 extends from another side of the nose 91, generally radially opposite one another, the nomenclature first and second being arbitrary. The first portion 92 extends along the configuration 90 and includes external ribbing, serrations, threading or the like 96 and terminates in a U member 97. The U member 97 provides a means for receiving a driver or driving tool for implanting the configuration 90. The second portion 93 extends along the configuration 90 and includes external ribbing, serrations, threading or the like 100 and terminates in a U member 101. The U member 101, along with U member 97, provides a means for receiving a driver or driving tool for implanting the configuration 90.

Figure 32:
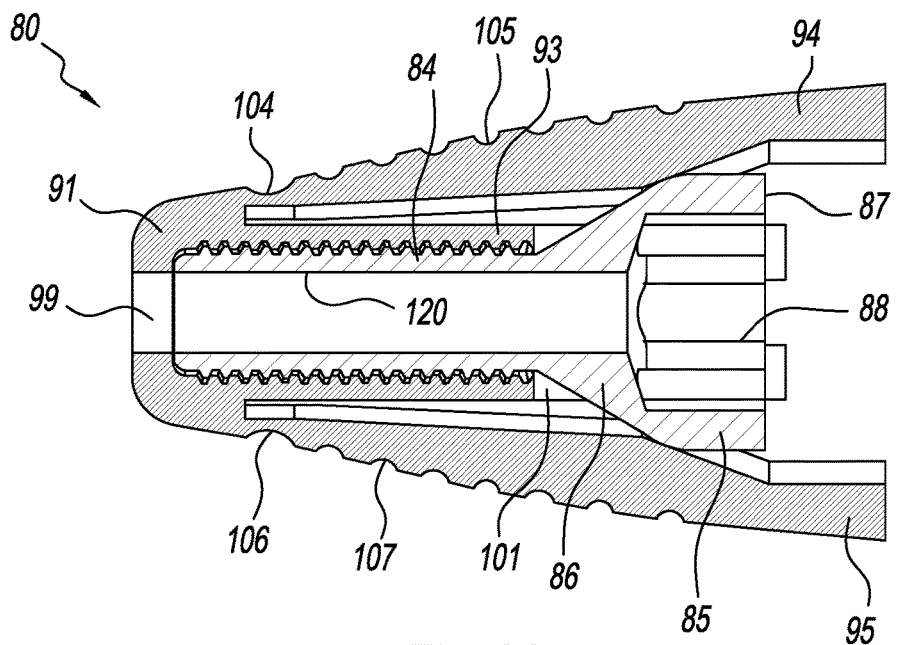
FIG. 32 is a sectional view of the expanded subtalar implant of FIG. 28 taken along line 32-32 of FIG. 30.
Figure 33:
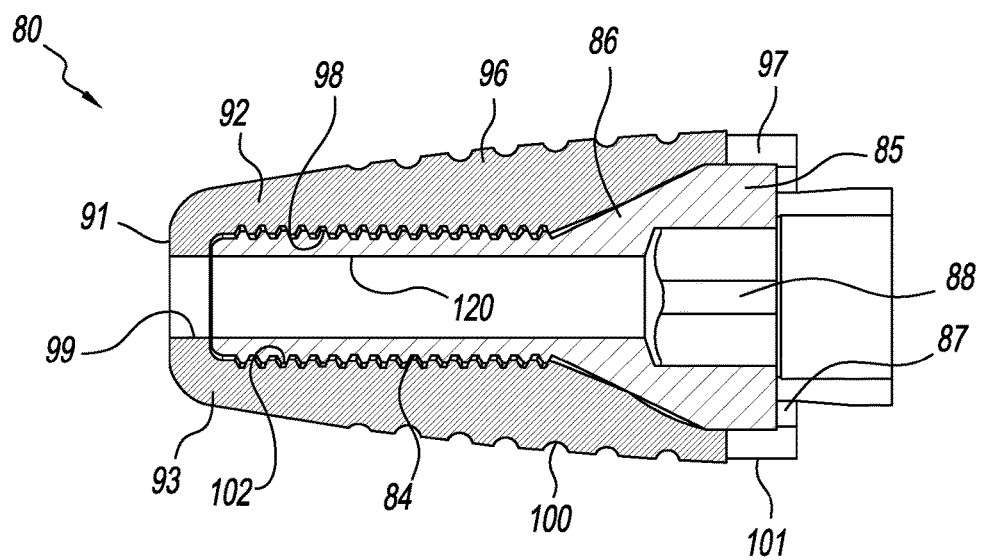
FIG. 33 is a sectional view of the expanded subtalar implant of FIG. 28 taken along line 33-33 of FIG. 29.

The configuration 90 further includes first and second expansion members, wings or the like 94, 95 that extend from the nose 91, the nomenclature first and second being arbitrary. A hinge 104 pivotally connects the first wing 94 to the nose 91, while a hinge 106 connects the second wing 95 to the nose 91. The hinges 104, 106 allow the wings 94, 95 to pivot relative to the remainder of the configuration 90. Insertion of the screw 82 causes the wings 94, 95 to pivot or expand outwardly from the configuration (see e.g., FIGS. 28-33). While two wings are shown, the subtalar implant 80 may have more than two expansion wings. The hinges 104, 106 are preferably, but not necessarily, fashioned out of the implant body so as to be integral therewith. The first wing 94 includes external ribbing, serrations, threading or the like 105, while the second wing 95 likewise includes external ribbing, serrations, threading or the like 107. The external ribbing, serrations, threading or the like of the first and second arms 92, 93 and wings 94, 95 provides a gripping surface, allows insertion of the configuration 90, and/or provides anti-back-out of the configuration 90. A bore 99 is provided in the nose 91 and extends through the implant 81. As seen in FIG. 33, the bore 99 provides communication with the internal bore or cannula 120 of the screw 82.

Figure 20:
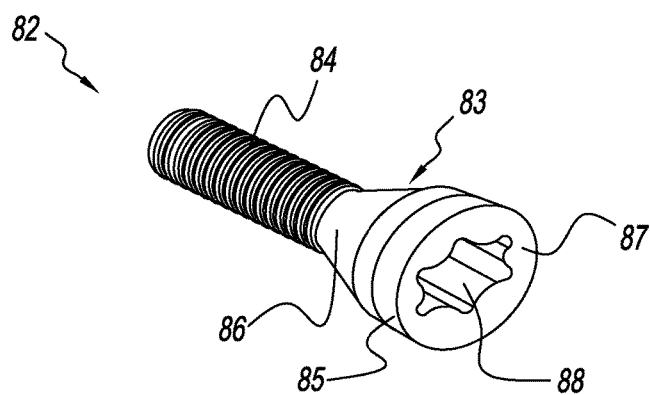
FIG. 20 is an isometric view of another component of the subtalar implant of FIG. 12.
Figure 21:
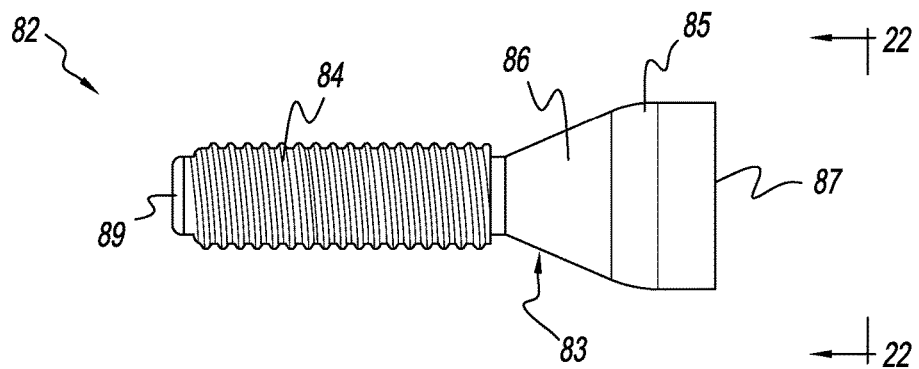
FIG. 21 is a side view of the component of FIG. 20.
Figure 22:
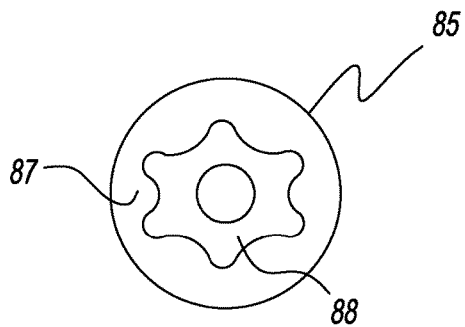
FIG. 22 is an end view of the component of FIG. 20 taken along line 22-22 of FIG. 21.
Figure 23:
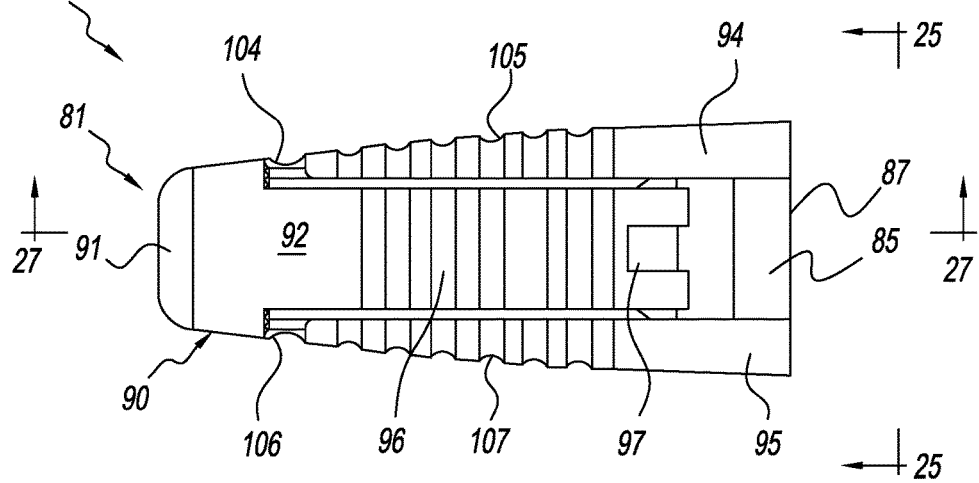
FIG. 23 is a side view of the subtalar implant of FIG. 12.
Figure 24:
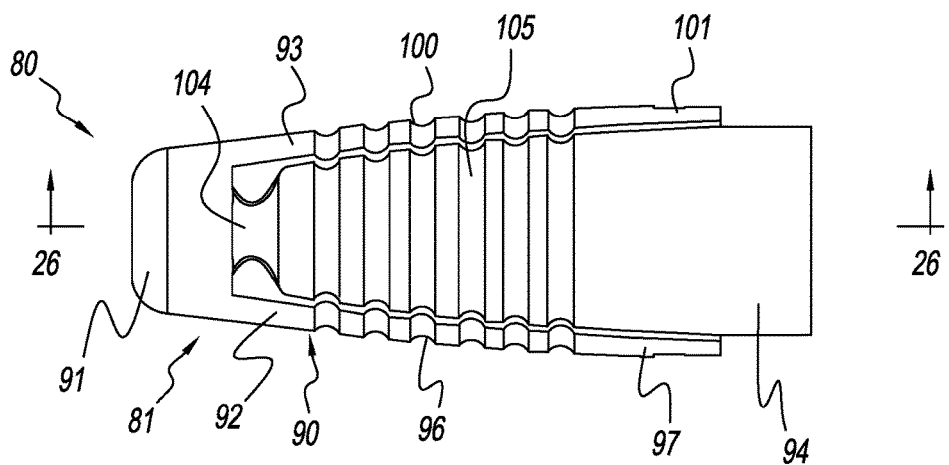
FIG. 24 is another side view of the subtalar implant of FIG. 12.
Figure 25:
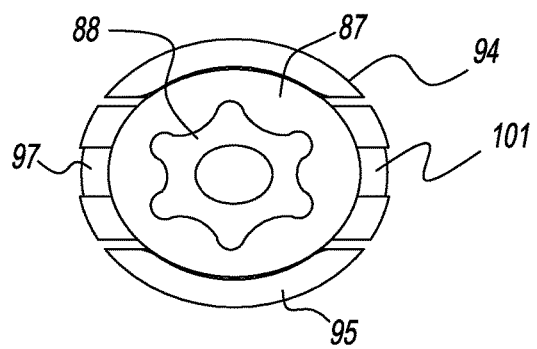
FIG. 25 is an end view of the subtalar implant of FIG. 12 taken along line 25-25 of FIG. 23.

The second component (i.e. expansion screw or member) 82 is shown in particular in FIGS. 20-22. The expansion screw is characterized by a body 83 having an externally threaded shank or shaft 84 with a head 85 at one end of the threaded shank 84 and an end 89 at the other end of the shank 84. The screw 82 is sized for reception in the implant body 81 as shown in other figures. The head 85 has a top 87 and transitions from the threaded shank 84 via an angled neck 86, the angled neck 86 and head 85 providing gradual expansion of the wings 94, 95 of the implant body 81 as it is threadedly (rotatably) inserted therein (see e.g., FIGS. 28-33).

Figure 26:
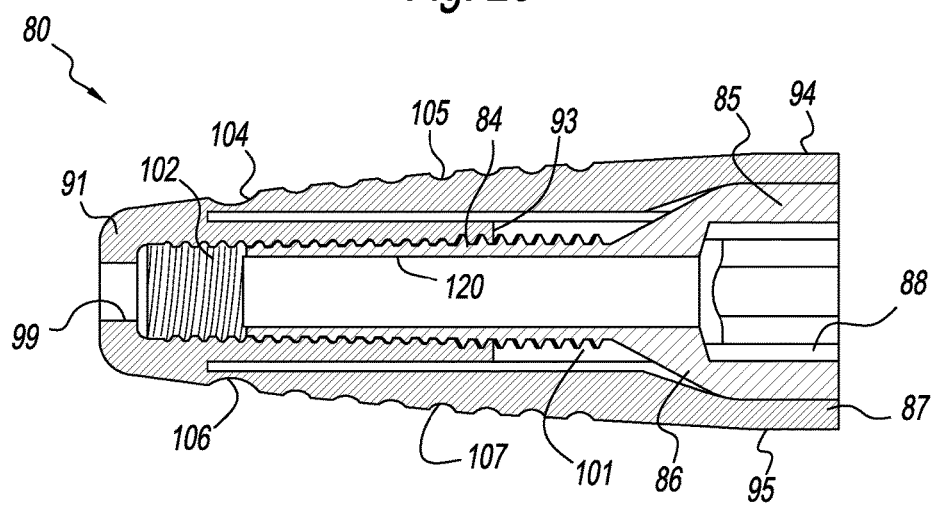
FIG. 26 is a sectional view of the subtalar implant of FIG. 12 taken along line 26-26 of FIG. 24.
Figure 27:
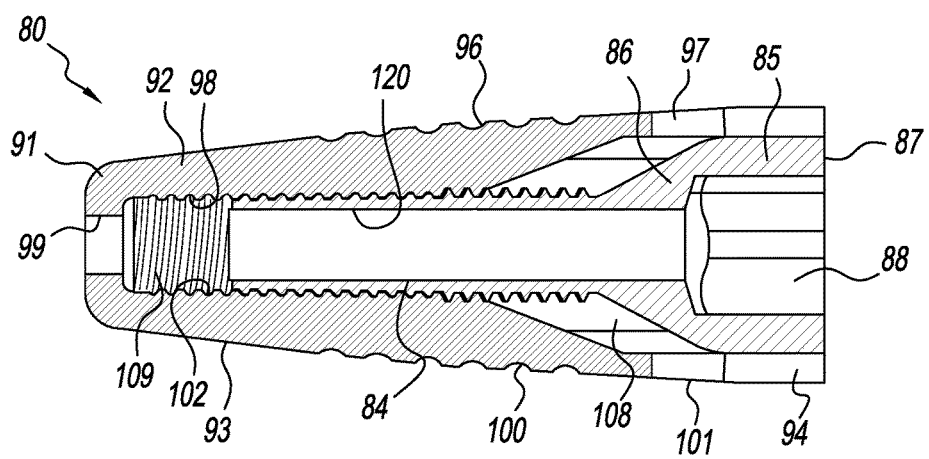
FIG. 27 is a sectional view of the subtalar implant of FIG. 12 taken along line 27-27 of FIG. 23.
Figure 28:
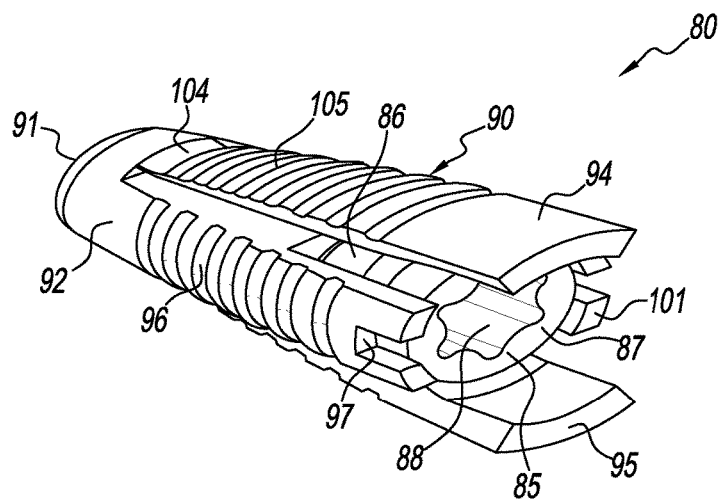
FIG. 28 is a rear isometric view of the subtalar implant of FIG. 12, the two expansion segments in an expanded state.
Figure 29:
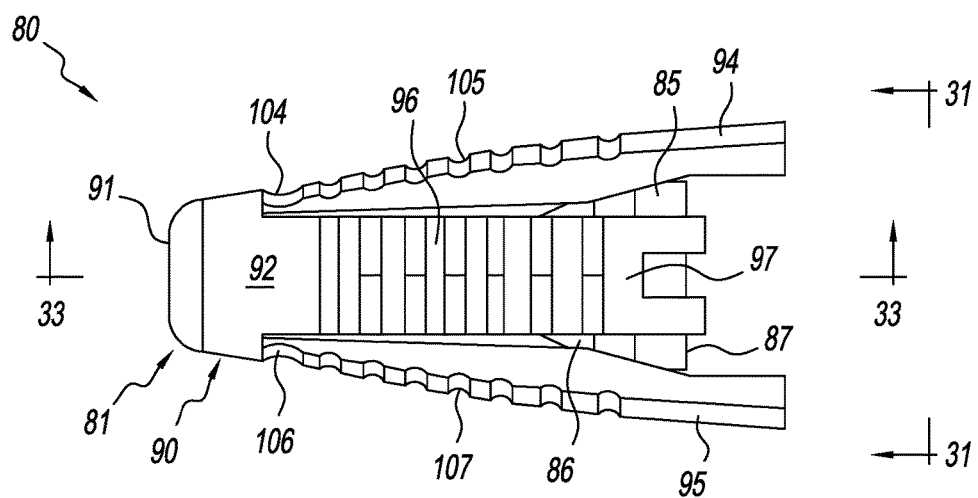
FIG. 29 is a side view of the expanded subtalar implant of FIG. 28.
Figure 30:
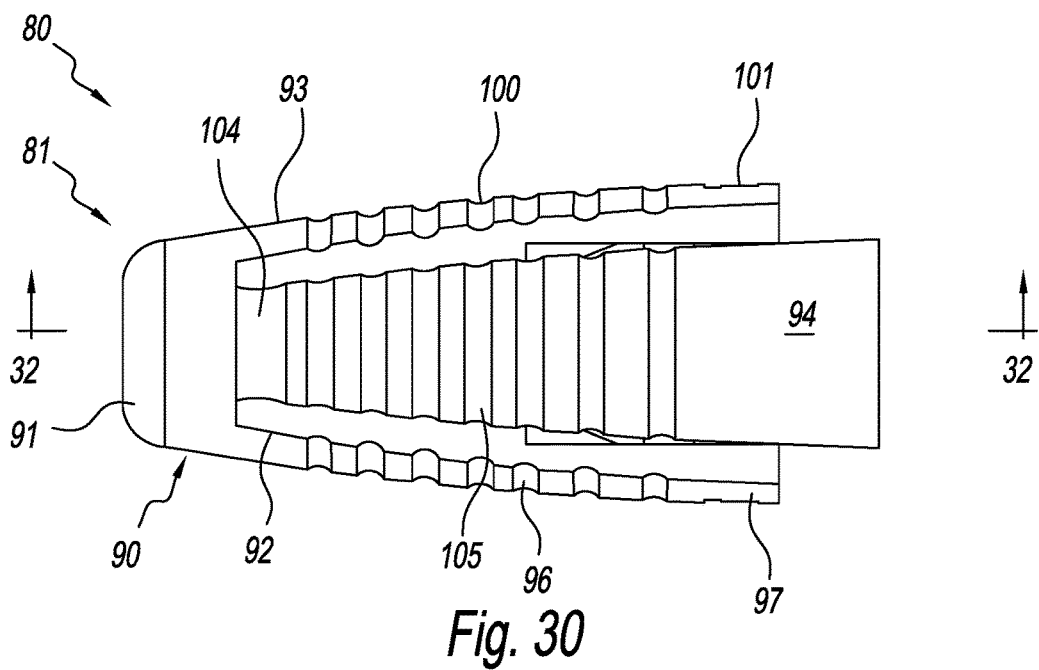
FIG. 30 is another side view of the expanded subtalar implant of FIG. 28.
Figure 31:
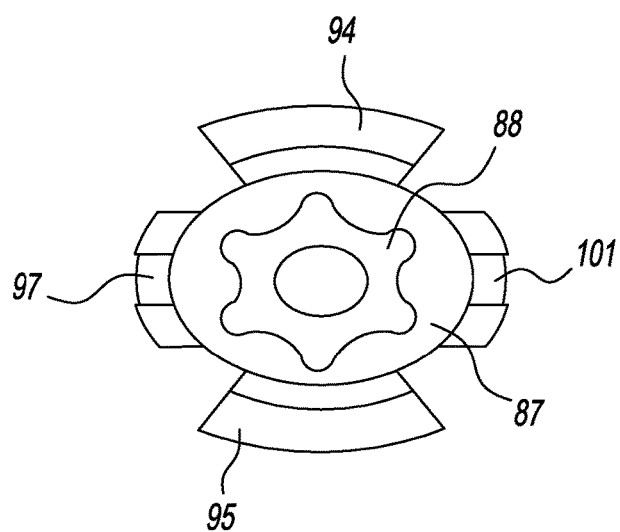
FIG. 31 is an end view of the expanded subtalar implant of FIG. 28 taken along line 31-31 of FIG. 29.

FIGS. 26 and 27 provide sectional views of the subtalar implant 80 with the expansion screw 82 beginning to be inserted into the configuration 81. At this point, the angled neck 86 of the head 85 of the expansion screw 82 has not yet reached the angled inside surfaces of the first and second wings 94, 95. Therefore, the wings have not yet begun to expand. FIGS. 32 and 33 provides sectional views of the subtalar implant 80 with the expansion screw 82 being threadedly received in the implant body 90. At this point, the angled neck 86 of the head 85 of the expansion screw 82 contacts the angled inside surfaces of the first and second wings 94, 95. Therefore, the wings expand. In all of the forms presented herein of a subtalar implant, the expansion segments, wings, portions or the like expand radially outwardly from the implant, particularly, but not necessarily from proximate a rear portion of the implant. Moreover, expansion is provided by either in internal, integral expansion mechanism or a separate device.

The present subtalar implant is used with and/or for subtalar arthroereisis and is thus intended to assist in treating the hyperpronated foot by stabilizing the subtalar joint. It is intended to block forward, downward, and medial displacement of the talus, thereby limiting excessive eversion of the hindfoot. The subtalar implant may also be used as an adjunct in conjunction with other corrective procedures, including posterior tibial tendon reconstruction, FDL tendon transfers and the medial displacement calcaneal osteotomy.

It should be appreciated that dimensions of the components, structures, and/or features of the present subtalar implants can be altered as desired.

What is claimed is:

1. A subtalar implant comprising:
an implant body having a first end and a second end;
a first segment coupled pivotally to the implant body and adapted to flex outwardly from the implant body upon application of a bias internal to the implant body;
a second segment coupled pivotally to the implant body and adapted to flex outwardly from the implant body upon application of the bias internal to the implant body; and
an expansion mechanism configured to provide the bias internal to the implant body through rotation of the expansion mechanism, the expansion mechanism comprising:
a threaded shaft coupled to the implant body and defining an axis;
an expander rotatably coupled to the threaded shaft and having internal threads;
wherein rotation of the expander and engagement between the internal threads and the threaded shaft causes the expander to move linearly along the axis and pivot the first segment and the second segment.

2. The subtalar implant of claim 1, wherein:
the first segment is pivotally coupled to the implant body by a first hinge located proximate the first end of the implant body; and
the second segment is pivotally coupled to the implant body by a second hinge located proximate the first end of the implant body.

3. The subtalar implant of claim 2, wherein:
the first hinge is integral with the implant body; and
the second hinge is integral with the implant body.

4. The subtalar implant of claim 2, wherein the expansion mechanism is integral with the implant body.

5. The subtalar implant of claim 1, wherein the first and second segments each includes internal threads, wherein the expander includes external threads that engage the internal threads of the first and second segments, wherein the engagement of external threads of the expander and the internal threads of the segments causes the segments to flex outwardly.

6. The subtalar implant of claim 1 wherein the threaded shaft is coupled to the implant body proximate the first end, and wherein expander is disposed proximate the second end of the implant body.

7. The subtalar implant of claim 1, wherein the expander is separate from the implant body.

8. The subtalar implant of claim 7, wherein the expander has a head having a non-threaded angled neck, the angled neck providing the bias internal to the implant body.

9. The subtalar implant of claim 1, wherein linear movement of the expander towards the first end causes the first segment and the second segment to flex outwardly.

10. The subtalar implant of claim 9, wherein linear movement of the expander towards the second end causes the first segment and the second segment to pivot inwardly.

11. An arthroereisis implant comprising:
an implant body having a first end and a second end;
a first segment coupled pivotally to the implant body by a first hinge and adapted to flex outwardly from the implant body upon application of a bias internal to the implant body;
a second segment coupled pivotally to the implant body by a second hinge and adapted to flex outwardly from the implant body upon application of the bias internal to the implant body; and
an expansion mechanism configured to provide the bias internal to the implant body through rotation of the expansion mechanism, the expansion mechanism comprising:
a threaded shaft coupled to the implant body and defining an axis;
an expander rotatably coupled to the threaded shaft;
wherein rotation of the expander on the threaded shaft in a first direction causes the expander to move linearly along the axis toward the first end and pivot the first segment and the second segment.

12. The arthroereisis implant of claim 11, wherein:
the first hinge located proximate the first end of the implant body; and
the second hinge located proximate the first end of the implant body.

13. The arthroereisis implant of claim 12, wherein:
the first hinge is integral with the implant body; and
the second hinge is integral with the implant body.

14. The arthroereisis implant of claim 13, wherein the expansion mechanism is integral with the implant body.

15. The arthroereisis implant of claim 11, wherein the first and second segments each includes internal threads, wherein the expander includes external threads that engage the internal threads of the first and second segments during rotation and linear movement of the expander.

16. The arthroereisis implant of claim 15, wherein the threaded shaft is connected to the implant body adjacent the first end, and wherein expander is disposed proximate the second end of the implant body.

17. The arthroereisis implant of claim 11, wherein the expander is separate from the implant body.

18. The arthroereisis implant of claim 17, wherein the expander has a head having non-threaded angled neck, the angled neck providing the bias internal to the implant body.

19. The arthroereisis implant of claim 11, wherein linear movement of the expander towards the first end causes the first segment and the second segment to flex outwardly.

20. The arthroereisis implant of claim 19, wherein linear movement of the expander towards the second end causes the first segment and the second segment to pivot inwardly.

* * * * *